(12) United States Patent
Cabaud et al.

(10) Patent No.: US 7,758,536 B2
(45) Date of Patent: Jul. 20, 2010

(54) SUBCUTANEOUS VALVE

(75) Inventors: François Cabaud, Chatillon le Duc (FR); Pascal Coneau, Etuz (FR); Philippe Negre, Paris (FR)

(73) Assignee: Sophysa, Orsay (FR)

( * ) Notice: Subject to any disclaimer, the term of this patent is extended or adjusted under 35 U.S.C. 154(b) by 1332 days.

(21) Appl. No.: 11/143,634

(22) Filed: Jun. 3, 2005

(65) Prior Publication Data

US 2005/0279960 A1 Dec. 22, 2005

(30) Foreign Application Priority Data

Jun. 11, 2004 (FR) .................................. 04 51264

(51) Int. Cl.
*A61M 5/00* (2006.01)
*F16K 5/00* (2006.01)
(52) U.S. Cl. .......................................... 604/9; 251/304
(58) Field of Classification Search ............ 604/288.01, 604/9, 288.02–288.04, 248; 137/535, 539, 137/539.5
See application file for complete search history.

(56) References Cited

U.S. PATENT DOCUMENTS

| | | | | |
|---|---|---|---|---|
| 4,443,214 A | * | 4/1984 | Marion | ........................ 604/9 |
| 4,615,691 A | * | 10/1986 | Hakim et al. | ................. 604/9 |
| 4,673,384 A | | 6/1987 | Marion | |
| 4,772,257 A | * | 9/1988 | Hakim et al. | ................. 604/9 |
| 4,857,061 A | * | 8/1989 | Miller | ....................... 604/207 |
| 5,637,083 A | | 6/1997 | Bertrand et al. | |
| 5,643,194 A | * | 7/1997 | Negre | ............................. 604/8 |
| 2002/0058901 A1 | * | 5/2002 | Marion | ......................... 604/9 |
| 2003/0163079 A1 | * | 8/2003 | Burnett | ......................... 604/9 |
| 2004/0010219 A1 | * | 1/2004 | McCusker et al. | ............ 604/9 |
| 2007/0004999 A1 | | 1/2007 | Miethke | |
| 2007/0093741 A1 | | 4/2007 | Miethke | |

FOREIGN PATENT DOCUMENTS

| | | |
|---|---|---|
| EP | 0 688 575 A1 | 12/1995 |
| EP | 1 205 210 A1 | 5/2002 |
| FR | 2 804 331 A1 | 8/2001 |

* cited by examiner

*Primary Examiner*—Kevin C Sirmons
*Assistant Examiner*—Maria E Doukas
(74) *Attorney, Agent, or Firm*—Oliff & Berridge, PLC

(57) ABSTRACT

A subcutaneous valve having a body defining a chamber and including an inlet orifice and an outlet orifice opening out into the chamber, a shutter member suitable for closing the inlet orifice, at least in part, a resilient return member configured to hold the shutter member against the inlet orifice to regulate the passage of liquid through said inlet orifice, and a rotor housed in the chamber having a cam-forming surface, the resilient return member bearing against the cam-forming surface of the rotor by forming a moving contact with this surface.

26 Claims, 3 Drawing Sheets

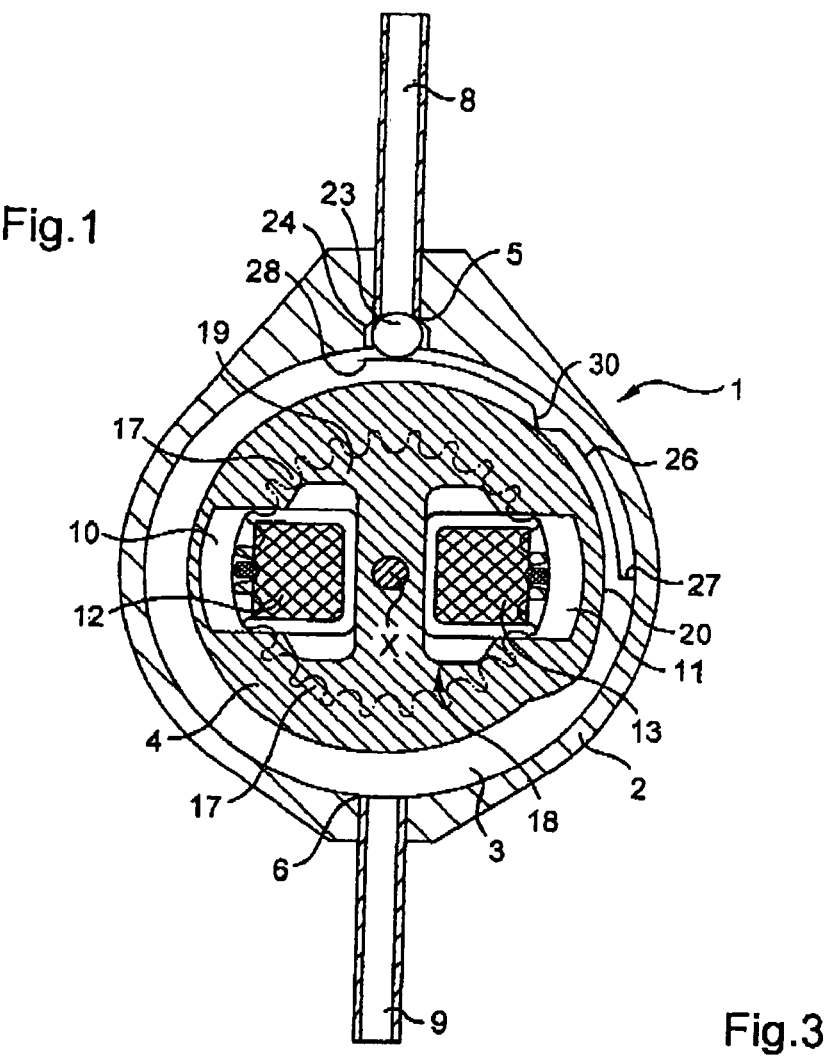
Fig.1
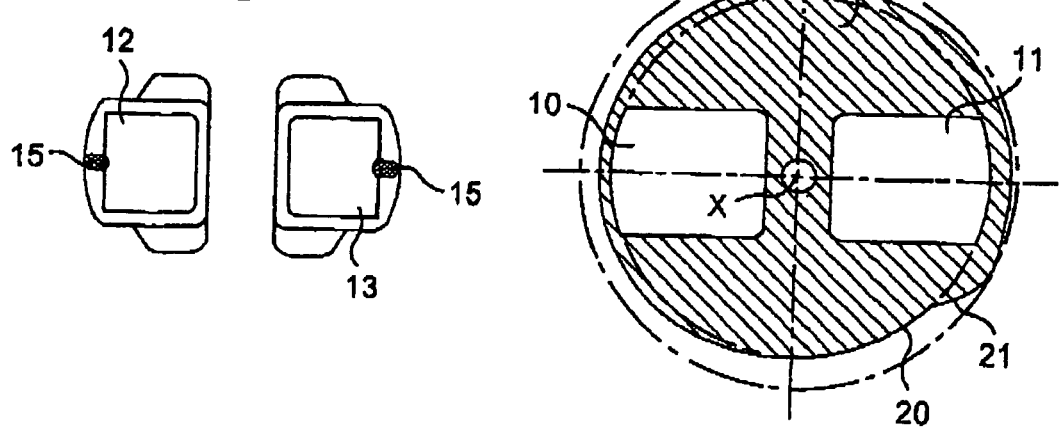
Fig.2
Fig.3

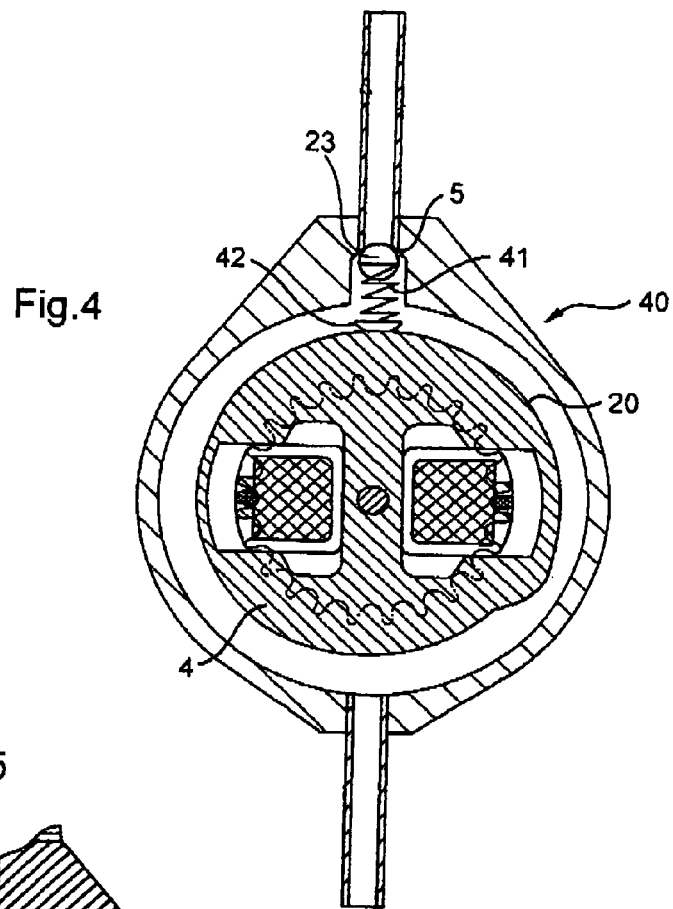
Fig.4
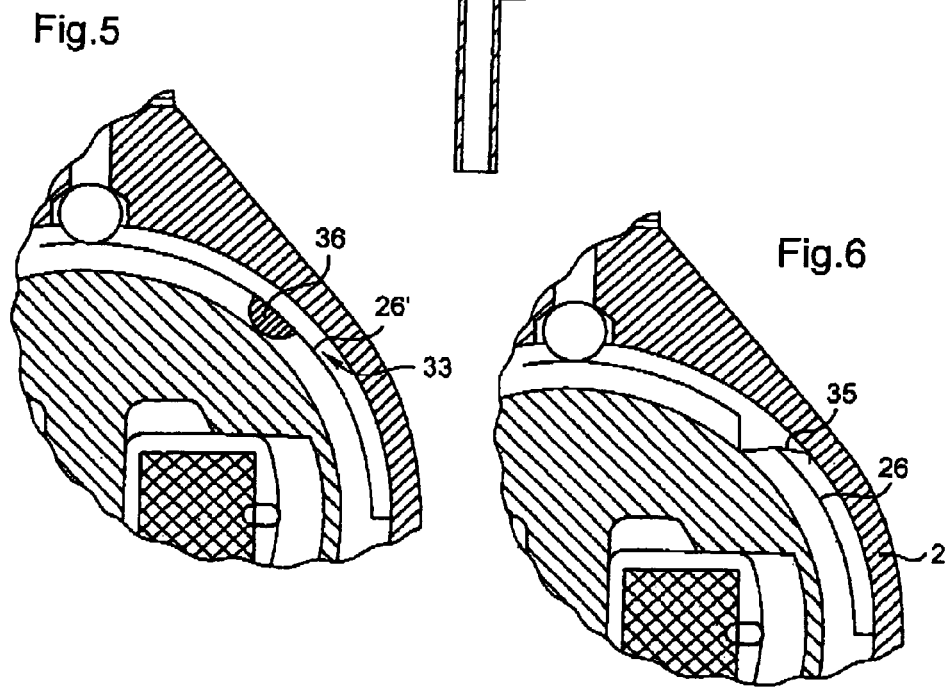
Fig.5
Fig.6

SUBCUTANEOUS VALVE

The present invention provides a subcutaneous valve for therapeutic applications, the valve being controllable from the outside through skin tissue in order to vary a liquid delivery or a passage in an implanted prosthesis or system.

BACKGROUND

Therapeutic applications include treating hydrocephaly by draining cerebrospinal fluid contained in ventricles within the skull cavity to some other site for resorption.

European patent EP-B1-0 688 575 in the name of the present Applicant discloses such a valve, including a rotor provided with a curved spring blade fixed thereover, the spring blade pressing against a ball to hold it against an inlet orifice of the valve so as to regulate the passage of fluid through said inlet orifice. Turning the rotor from one angular indexing position to another causes the point of contact of the ball on the spring blade to slide, and thus varies the stress exerted by the spring blade on the ball. The rotor can be locked and unlocked by mutual attraction and/or repulsion of micromagnets placed on the rotor.

SUMMARY

The invention seeks to improve a subcutaneous valve of the above-specified type.

Thus, the invention provides a subcutaneous valve comprising:
  a body defining a chamber and including an inlet orifice and an outlet orifice opening out into the chamber;
  a shutter member suitable for closing the inlet orifice, at least in part;
  a resilient return member arranged to hold the shutter member against the inlet orifice so as to regulate the passage of liquid through said inlet orifice; and
  a rotor housed in the chamber;
  wherein the rotor has a cam-forming surface, and wherein the resilient return member bears against said surface of the rotor by forming a moving contact with said surface.

By means of the invention, the resilient return member can be independent of the rotor, i.e. it does not need to be fixed thereto. The structure of the rotor can thus be relatively simple, and in particular the rotor can have a small number of component parts.

Furthermore, when the resilient return member comprises a spring blade, its length can be short, e.g. extending over an angular sector of less than 180°, e.g. substantially equal to 90°. In the invention, the spring blade is not fastened to the rotor and the shutter member does not need to slide relative to the spring blade.

In addition, the invention enables the stress exerted by the resilient return member on the shutter member to be adjusted relatively accurately because of the presence of the cam-forming surface.

Advantageously, the resilient return member is arranged to enable it to bear continuously against the cam-forming surface of the rotor.

In an embodiment of the invention, the resilient return member is fastened, in particular at one end, to the body of the valve.

The resilient return member may comprise a spring blade, in particular a curved spring blade, having a free end that comes to bear against the shutter member with predetermined stress.

The spring blade may advantageously include a projecting portion that comes to bear against the cam-forming surface.

In a variant, the resilient return member comprises a bearing element fastened to the spring blade and suitable for sliding on the cam-forming surface.

Because of the above-mentioned bearing element or projecting portion of the spring blade, turning the rotor causes the spring blade to be deflected, thereby enabling the stress exerted on the shutter member by the spring blade to be modified.

The shape of the cam-forming surface is selected as a function of a desired range of stresses that it is desired to exert on the shutter member.

The spring blade may advantageously exert stress on the above-mentioned bearing element or projecting portion in such a manner as to ensure continuous contact between the cam-forming surface and said bearing element or projecting portion.

The resilient return member may comprise a single spring blade. In a variant, the resilient return member may include an additional spring blade, arranged specifically to increase the stress exerted on the bearing element or the projecting portion of the spring blade against the cam-forming surface. The resilient return member may comprise two assembled-together spring blades, for example.

In another embodiment of the invention, the resilient return member is independent of the valve body, i.e. it is not fastened to the body.

The resilient return member may comprise a spring, in particular a helical spring, having one end secured to a bearing element suitable for sliding on the cam-forming surface, and having the other end of the spring bearing in particular against the shutter member.

In an embodiment of the invention, an additional spring is disposed between the bearing element and the valve body or an insert fastened to said body.

The spring bearing against the shutter member may be disposed in such a manner as to be surrounded by the additional spring, for example.

The bearing element may be constituted by a portion of a cage provided with one or more orifices forming a passage between the above-mentioned inlet orifice and the inside of the valve.

Advantageously, the cam-forming surface extends over the entire periphery of the rotor.

The invention thus enables a relatively broad range of pressures or constraints to be achieved since the range of angular indexing positions for the rotor can extend from 0 to 360°.

In an embodiment of the invention, the cam-forming surface presents a radius that increases over an angular sector of more than 180°, in particular substantially equal to 360°.

The cam-forming surface may be substantially continuous or it may include at least one setback or notch, and in particular it may include a plurality of setbacks or notches distributed around the axis of rotation of the rotor, and into which a portion of the resilient return member can engage. These setbacks correspond advantageously to angular indexing positions of the rotor.

The shutter member advantageously comprises a ball.

Also preferably, the rotor has two micromagnets that are movable linearly relative to the rotor in a direction that is substantially radial, and suitable for co-operating with means for locking the rotor in a predetermined angular position.

In an embodiment of the invention, the height of the gravity center of the rotor measured along an axis perpendicular to the rotor is constant when the rotor is rotated.

BRIEF DESCRIPTION OF THE DRAWINGS

The invention can be better understood on reading the following detailed description of non-limiting embodiments of the invention, and on examining the accompanying drawings, in which:

FIG. 1 is a diagrammatic and fragmentary axial section view of a subcutaneous valve in accordance with the invention;

FIG. 2 is a diagrammatic and fragmentary view of two micromagnets for fitting to the FIG. 1 valve;

FIG. 3 is a diagrammatic and fragmentary axial section view of the rotor of the FIG. 1 valve;

FIG. 4 is a diagrammatic and fragmentary axial section view of a valve constituting another embodiment of the invention; and FIGS. 5 to 9 are diagrammatic and fragmentary views showing other variant embodiments of the invention.

MORE DETAILED DESCRIPTION

Figure 7:
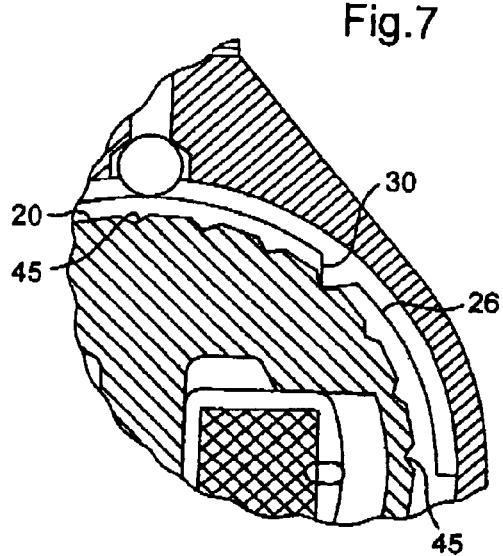

FIG. 1 shows a subcutaneous valve 1 in accordance with the invention comprising a body 2 defining a substantially cylindrical chamber 3 of axis X in which a rotor 4 is housed.

The body 2 has inlet and outlet orifices 5 and 6 opening out into the chamber 3.

An inlet duct 8 and an outlet duct 9 are secured to the body 2 and open out respectively into the inlet and outlet orifices 5 and 6.

The inlet duct 8 and the outlet duct 9 may be connected respectively to a feed catheter and to a liquid drain catheter (not shown in the figures).

The rotor 4 includes two housings 10 and 11 each suitable for receiving a respective micromagnet 12 or 13.

Each micromagnet 12, 13 is arranged to be capable of sliding linearly in the corresponding housing 10, 11 in a direction that is substantially radial. Each of these micromagnets 12, 13 includes a locking portion in relief 15, as shown in FIG. 2.

By way of example, these locking portions in relief 15 may comprise respective cylindrical studs.

These portions in relief 15 are suitable for engaging in notches 17 of locking means 18 of the valve 1.

In the example described, these locking means 18 comprise a central portion 19 that is stationary relative to the body 2, and in the periphery of which the notches 17 are formed. These notches are regularly distributed all around the axis X.

By using an external adjustment device (not shown in the figures), it is possible to move the micromagnets 12 and 13 simultaneously in their respective housings 10 and 11 in a radially outward direction in order to disengage the portions in relief 15 form the notches.

This disengagement allows the rotor 4 to turn about the axis X from one angularly indexed position towards another.

The external adjustment device also enables the micromagnets 12 and 13 to be repositioned in a locking position in which the portions in relief 15 are engaged in the notches 17.

Reference can be made to patent No. EP-B1-0 688 575 for more details about the structure of the external adjustment device.

The rotor 4 has a cam-forming surface 20 around its entire periphery.

As can be seen in FIG. 3 in particular, this surface 20 presents a radius that increases in a clockwise direction over an angular sector that is substantially equal to 360° C., and it includes a short zone 21 presenting a relatively steep slope of decreasing radius.

The valve 1 includes a shutter member 23 constituted by a ball which is held against a frustoconical seat 24 facing the inlet orifice 5.

The shutter member 23 is held against this inlet orifice 5 by means of a resilient return member 26.

In the example described, the resilient return member 26 is a curved spring blade having one end 27 fastened to a side wall of the a valve body 2, and having a free end 28 bearing against the shutter member 23. The resilient return member 26 may have first and second faces, the first face bearing against the cam-forming surface 20 of the rotor 4 by forming a moving contact with the cam-forming surface and the second face of the resilient return member 26 is arranged to hold the shutter member 23 against the inlet orifice 5.

The spring blade 26 also includes a projecting portion 30 that comes into contact with the cam-forming surface 20 of the rotor 4, as can be seen in FIG. 1. This portion 30 may be provided by folding the spring blade, for example.

The spring blade 26 is arranged to press via its projecting portion 30 against the cam-forming surface 20 with a certain amount of stress. The portion 30 forms a moving contact with the cam-forming surface 20 such that the distance between the moving contact and the axis of rotation of the rotor may be variable.

To increase this stress applied by the spring blade 26 against the surface 20, and as shown in FIG. 6, it is possible to provide an additional spring blade 35 which bears against the side wall of the chamber 3.

When the angular position of the rotor 4 is changed, the cam-forming surface 20 deflects the spring blade 26 and consequently modifies the stress said spring blade 26 exerts on the shutter member 23.

In the examples described above, contact between the resilient return member 26 and the cam-forming surface 20 is achieved via a portion of the spring blade 26 itself.

In a variant, and as shown in FIG. 5, the resilient return member 33 includes a bearing element 36 that is fastened to the spring blade 26'.

By way of example, this bearing element 36 may be made of a plastics material, a metal, or a hard material, and it may be assembled to the spring blade 26'.

FIG. 4 shows a valve 40 constituting another embodiment of the invention. The valve 40 differs from the valve 1 described above by the fact that the shutter member 23 is held against the inlet orifice 5, no longer by a spring blade, but by means of a helical spring 41 having one end bearing against the shutter member 23 and its other end secured to a bearing element 42 that is suitable for sliding over the cam-forming surface 20 of the rotor 4. This bearing element 42 may be made of a plastics material, a metal, or a hard material.

By modifying the angular position of the rotor 4, the surface 20 exerts a variable amount of stress on the helical spring 41 so as to modify the pressure it exerts on the shutter member 23.

Figure 9:
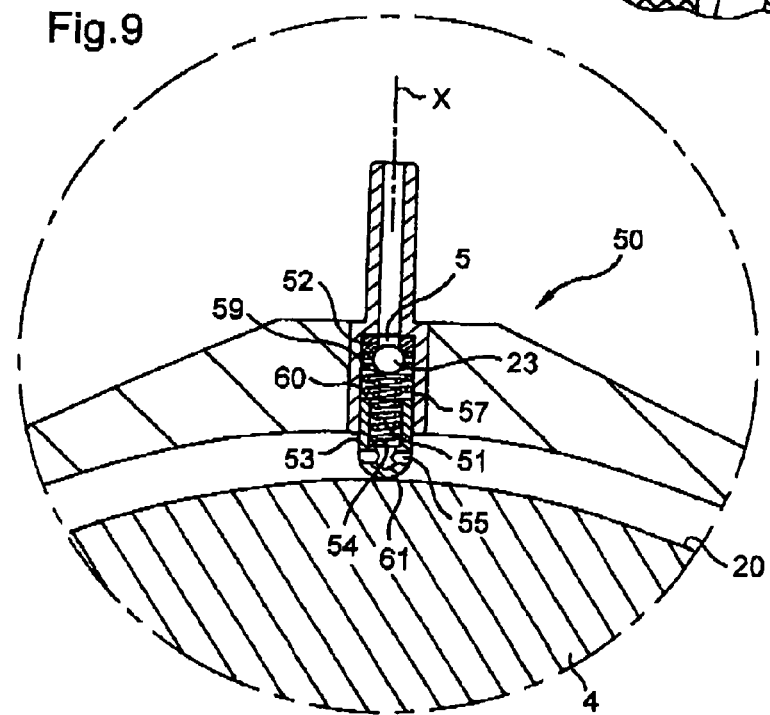

FIG. 9 shows a subcutaneous valve 50 constituting another embodiment of the invention.

Like the example described above with reference to FIG. 4, the valve 50 has a shutter member 23 held against the inlet orifice 5 so as to press against a seat 52, under thrust from a first spring 51, in particular a helical spring.

The bottom end of the first spring 51 presses against a shoulder 54 of a cage 53.

The cage 53 has a plurality of orifices 55 leaving a passage for a flow to pass between the inlet orifice 5 and the inside of the valve 50.

The cage 53 is mounted to slide along an axis X in a housing 57.

The cage 53 is pushed against the cam-forming surface 20 of the rotor 4 via a second spring 59, in particular a helical spring disposed between the end of the housing 57 and the top end 60 of the cage 53.

The second spring 59 presents an inside diameter that is large enough to be capable of receiving the first spring 51.

The cage 53 has a bottom portion 61 that is substantially hemispherical, for example, constituting a bearing element that comes into contact with the cam-forming surface 20 of the rotor 4.

The disposition of the two springs 51 and 59 enables the stress exerted by the bearing element 61 on the cam-forming surface 20 to be increased.

In the examples described above, the cam-forming surface 20 is substantially continuous, i.e. it does not include any notches.

Figure 8:
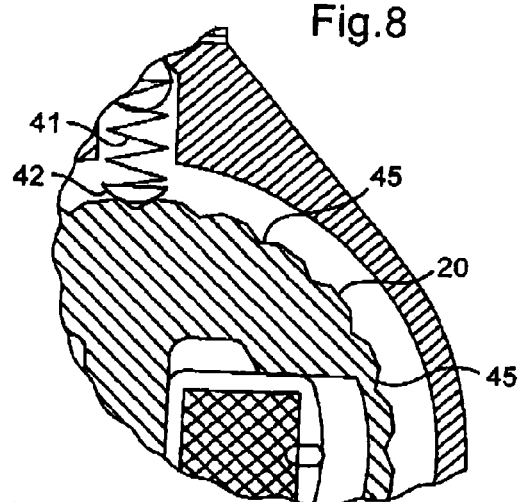

It would not go beyond the ambit of the present invention for the cam-forming surface 20 to present a plurality of notches 45, e.g. regularly distributed around the axis X, as shown in FIGS. 7 and 8.

The notches 45 may be configured so as to correspond to angular indexing positions for the rotor 4 in the body 2.

As shown in FIG. 7, the resilient return member is constituted by a spring blade 26, and this spring blade may have a projecting portion 30 suitable for engaging in notches 45.

As shown in FIG. 8, when the resilient return member includes a bearing element 42 that is fastened to a helical spring 41, the bearing element 42 may be arranged to engage in a notch 45 of the rotor 4.

Naturally, the invention is not limited to the embodiments described above.

In particular, it could have a cam-forming surface that extends over an angular sector that is less than 360°, for example over an angular sector of about 180°.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A subcutaneous valve comprising:
a body defining a chamber and comprising an inlet orifice and an outlet orifice opening out into the chamber;
a shutter member suitable for closing the inlet orifice, at least in part;
a resilient return member configured to hold the shutter member against the inlet orifice so as to regulate the passage of liquid through said inlet orifice; and
a rotor housed in the chamber;
wherein:
the rotor has a cam-forming surface,
the resilient return member bears against said surface of the rotor by forming a moving contact with said surface, and
a distance between said moving contact and an axis of rotation of the rotor is variable.

2. A valve according to claim 1, wherein the resilient return member is secured to the valve body.

3. A valve according to claim 1, wherein the resilient return member comprises a curved spring blade.

4. A valve according to claim 3, wherein the spring blade comprises a projecting portion which comes to bear against the cam-forming surface.

5. A valve according to claim 3, wherein the resilient return member comprises a first element fastened to the spring blade and suitable for sliding on the cam-forming surface.

6. A valve according to claim 3, wherein the resilient return member comprises a single spring blade.

7. A valve according to claim 3, wherein the resilient return member comprises at least two assembled-together spring blades.

8. A valve according to claim 1, wherein the resilient return member is independent of the valve body.

9. A valve according to claim 8, wherein the resilient return member comprises a spring.

10. A valve according to claim 9, wherein an additional spring is disposed between a bearing element suitable for sliding on the cam-forming surface of the rotor and the valve body or an insert fastened to the body.

11. A valve according to claim 1, wherein the cam-forming surface extends around the entire periphery of the rotor.

12. A valve according to claim 1, wherein the cam-forming surface presents a radius that increases over an angular sector of more than 180°.

13. A valve according to claim 1, wherein the cam-forming surface includes at least one setback in which a portion of the resilient return member can be engaged.

14. A valve according to claim 1, wherein the shutter member comprises a ball.

15. A valve according to claim 1, wherein the rotor includes two micromagnets that are movable linearly relative to the rotor in a direction that is substantially radial, and that are suitable for co-operating with means for locking the rotor in a predetermined angular position.

16. A valve according to claim 2, wherein the resilient return member is secured to the valve body via one end.

17. A valve according to claim 9, wherein the resilient return member comprises a helical spring.

18. A valve according to claim 9, wherein the resilient return member is secured at one end to a bearing element suitable for sliding on the cam-forming surface, with the other end of the spring bearing against the shutter member.

19. A valve according to claim 12, wherein the cam-forming surface presents a radius that increases over an angular sector substantially equal to 360°.

20. A valve according to claim 13, wherein the cam-forming surface includes a plurality of setbacks distributed all around the axis of rotation of the rotor.

21. A subcutaneous valve comprising:
a body defining a chamber and comprising an inlet orifice and an outlet orifice opening out into the chamber;
a shutter member suitable for closing the inlet orifice, at least in part;
a resilient return member configured to hold the shutter member against the inlet orifice so as to regulate the passage of liquid through said inlet orifice; and
a rotor housed in the chamber;
wherein:
the rotor has a cam-forming surface,
the resilient return member bears against said surface of the rotor by forming a moving contact with said surface, and
the rotor includes two micromagnets that are movable linearly relative to the rotor in a direction that is substantially radial, and that are suitable for co-operating with means for locking the rotor in a predetermined angular position.

22. A subcutaneous valve comprising:

a body defining a chamber and comprising an inlet orifice and an outlet orifice opening out into the chamber;

a shutter member suitable for closing the inlet orifice, at least in part;

a resilient return member configured to hold the shutter member against the inlet orifice so as to regulate the passage of liquid through said inlet orifice; and a rotor housed in the chamber;

wherein:

the rotor has a cam-forming surface, the resilient return member bears against said surface of the rotor by forming a moving contact with said surface, the resilient return member is secured to the valve body via one end, and the moving contact is situated between a fixation point of the resilient return member to the valve body and a contact point between the resilient return member and the shutter member.

23. A valve according to claim 1, wherein the force exerted by the resilient return member on the shutter member increases with said distance.

24. A valve according to claim 3, wherein the resilient return member is a curved spring blade having one end fastened to a side wall of the valve body and having a free end bearing against the shutter member.

25. A valve according to claim 4, wherein the projecting portion is provided by folding the spring blade.

26. A valve according to claim 1, wherein the resilient return member comprises first and second faces, the first face bearing against said surface of the rotor by forming a moving contact with said surface and the second face of the resilient return member being arranged to hold the shutter member against the inlet orifice.

* * * * *